United States Patent [19]
Ho et al.

[11] Patent Number: 5,847,253
[45] Date of Patent: Dec. 8, 1998

[54] ALKYLATION-TRANSALKYLATION PROCESS USING STRIPPING TO PRODUCE A DRY TRANSALKYLATION FEED

[75] Inventors: Perry K. Ho, Wheeling; Constante P. Tagamolila, Arlington Heights, both of Ill.

[73] Assignee: UOP LLC, Des Plaines, Ill.

[21] Appl. No.: 819,827

[22] Filed: Mar. 18, 1997

Related U.S. Application Data

[60] Provisional application No. 60/014,737 Apr. 1, 1996.
[51] Int. Cl.[6] .................................................... C07C 2/66
[52] U.S. Cl. ...................... 585/450; 585/312; 585/314; 585/316; 585/323; 585/467; 585/475
[58] Field of Search .................................... 585/312, 314, 585/316, 323, 403, 444, 450, 467, 475

[56] References Cited

U.S. PATENT DOCUMENTS

| | | | |
|---|---|---|---|
| 2,787,648 | 4/1957 | King | 260/671 |
| 3,520,945 | 7/1970 | DeGraff | 260/671 |
| 3,674,885 | 7/1972 | Griesinger et al. | 260/671 B |
| 4,051,191 | 9/1977 | Ward | 260/671 R |
| 4,695,665 | 9/1987 | DeGraff | 585/450 |
| 5,030,786 | 7/1991 | Shamshoum et al. | 585/467 |
| 5,177,285 | 1/1993 | Van Opdorp et al. | 585/467 |
| 5,336,821 | 8/1994 | DeGraff et al. | 585/402 |

OTHER PUBLICATIONS

"Catalytic Distillation Route for Cumene" (pp. Q–1–Q–28) Presented to 1993 Dewitt Petrochemical Review in Houston, Texas; Mar. 23–25, 1993; by Angel Sy, Technology Manager; L. Smith, J. Chen, and F. Dautzenberg of CDTech; Houston, Texas.

"A New Highly Selective Zeolite Technology for Cumene" (pp. P–1–P–13) Presented to 1993 Dewitt Petrochemical Review; in Houston, Texas; Mar. 23–25, 1993; by Agustin Hernandez–Robinson, Senior Process Design Supervisor, Badger Engineers, Inc., Cambridge, Massachusetts and C. Morris Smith, Assistant Manager, Licensing, Mobil Research and Development Corporation, Princeton/Paulsboro, New Jersey.

"A New Highly Selective Zeolite Catalyst for Cumene Production" Presented to the Worldwide Solid Acid Process Conference; in Houston, Texas; Nov. 14–16, 1993; by Agustin Hernandez–Robinson, Manager, Cumene Technology and Sanjeev Ram, Manager, Styrene Technology; Badger Technology Center, Raytheon Engineers & Constructors; Cambridge, Massachusetts and C. Morris Smith, Assistant Manager—Licensing, Mobil Reserach and Development Corporation, Princeton/Paulsboro New Jersey.

*Primary Examiner*—Glenn Caldarola
*Assistant Examiner*—Thuan D. Dang
*Attorney, Agent, or Firm*—Thomas K. McBride; John F. Spears, Jr.; Michael A. Moore

[57] ABSTRACT

A process for the production of alkylaromatic hydrocarbons that operates with a high water content in an alkylation zone and a low water content in a transalkylation zone is disclosed. An aromatic feed and an acyclic feed are first passed through the alkylation reaction zone that operates at a high water content. A stripping column receives the effluent of the alkylation reaction zone, removes water and unreacted aromatic feed and produces a bottom stream containing unreacted aromatic feed and alkylated aromatics. A recycle column receives the bottom stream and produces an overhead stream of unreacted aromatic feed having a low water content. The overhead stream and a stream of polyalkylated aromatics are contacted in the transalkylation zone.

20 Claims, 1 Drawing Sheet

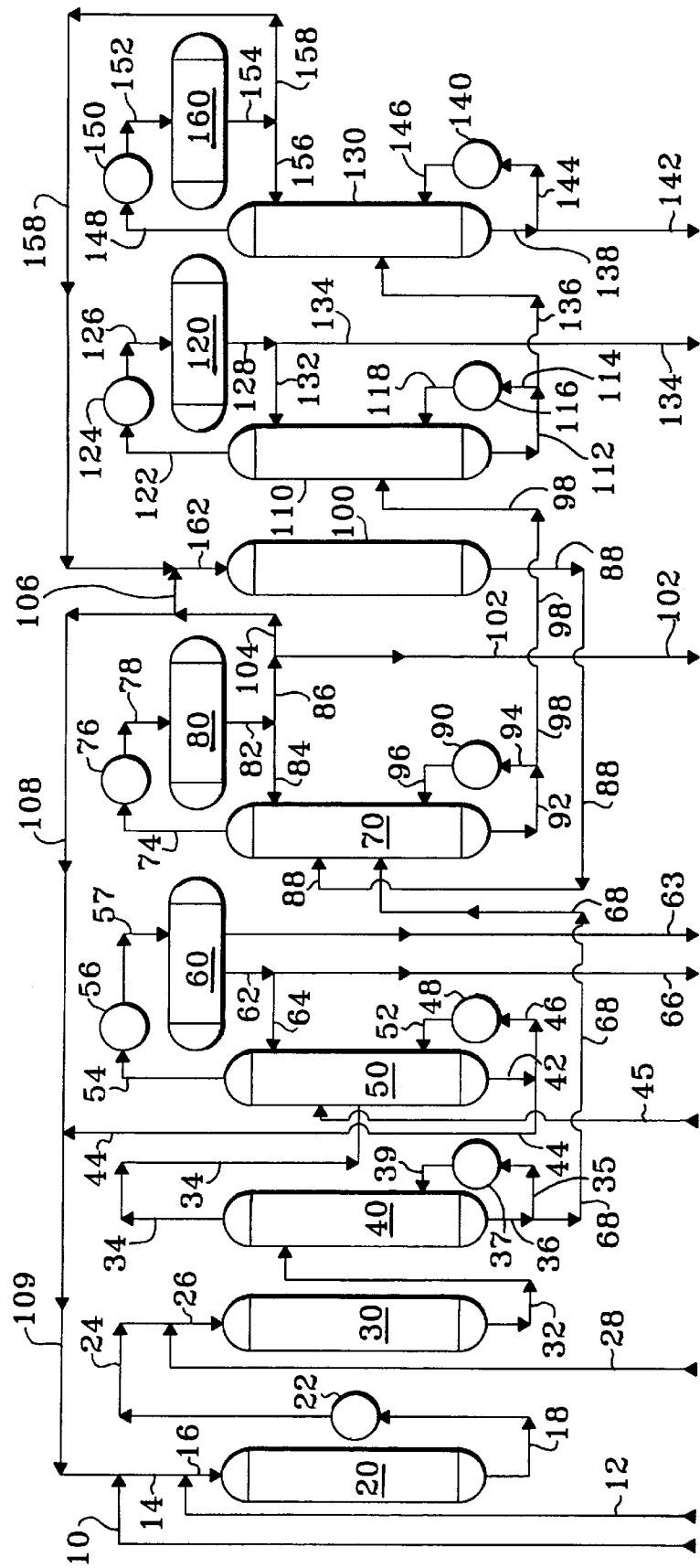

ALKYLATION-TRANSALKYLATION PROCESS USING STRIPPING TO PRODUCE A DRY TRANSALKYLATION FEED

CROSS-REFERENCE TO RELATED APPLICATION

This application claims the benefit of U.S. Provisional Application No. 60/014,737, filed on Apr. 1, 1996.

FIELD OF THE INVENTION

This invention relates to the production of alkylaromatic hydrocarbons by the reaction of an aromatic feed hydrocarbon and an acyclic olefinic hydrocarbon.

BACKGROUND OF THE INVENTION

The alkylation of aromatic hydrocarbons such as benzene using solid catalyst is a well-developed art which is practiced commercially in large scale industrial units. One commercial application of this process is the alkylation of benzene with propylene to produce cumene (isopropylbenzene), which is subsequently used in the production of phenol and acetone. Another application is the alkylation of benzene with ethylene to produce ethylbenzene, which is subsequently used to produce styrene. Persons of ordinary skill in the art are therefore familiar with the general design and operation of such alkylation processes.

The performances of aromatic alkylation processes are influenced by the stability and activity of the catalyst in the operating environment of the process. Currently available catalysts for the alkylation of aromatic hydrocarbons include solid phosphoric acid (SPA) catalysts and zeolite-containing catalysts. Zeolitic catalysts have certain advantages, such as greater catalytic activity for alkylation, over SPA catalysts. However, both SPA and zeolitic catalysts typically provide a relatively low aromatics conversion. This stems in part from the need to maintain a high ratio of aromatic feed hydrocarbon to alkenes that improves the selectivity of the alkylation catalyst for the desired monoalkylated products. Although SPA catalysts generally produce a relatively small amount of polyalkylated aromatic by-products, zeolitic catalysts generally produce a relatively large amount of polyalkylated aromatic by-products. This disadvantageous characteristic of zeolitic catalysts, however, can be overcome by contacting the polyalkylated aromatic by-products with additional feed aromatic hydrocarbon over a transalkylation catalyst. Therefore, alkylation processes in general, and zeolitic alkylation processes in particular, will typically have an alkylation reaction zone and a transalkylation reaction zone.

One method of improving the stability and yields of an alkylation-transalkylation process for producing monoalkylated aromatics is to operate the alkylation reaction zone at a relatively high water concentration and to operate the transalkylation reaction zone at a relatively low water concentration. U.S. Pat. No. 5,177,285 issued to Van Opdorp et al. discloses such an operation. However, if the alkylation reaction zone operates at a significantly higher water concentration than the transalkylation reaction zone, and if the alkylation reaction zone effluent contains a high ratio of unconverted aromatic feed hydrocarbon to aromatic product alkylate, then the recovery of the unconverted aromatic feed hydrocarbon from the alkylation reaction effluent must separate water from the aromatic feed hydrocarbon in order for a portion of the aromatic feed hydrocarbon from the alkylation reaction effluent to be passed to the transalkylation reaction zone.

One common arrangement for the recovery of aromatic feed hydrocarbon from a SPA alkylation reaction effluent uses a rectifier. Rectifiers are commonly used in many industrial alkylation processes that use a Friedel-Crafts type of catalyst such as aluminum chloride or solid phosphoric acid (SPA). SPA catalysts generally require a relatively high operating temperature. Although this characteristic feature of SPA alkylation catalyst is disadvantageous from a catalytic viewpoint, it is an advantage from an energy-utilization viewpoint. This is because a higher reaction temperature generally also means that the temperature of the reactor effluent is higher too, and therefore the options for using the energy of the reactor effluent in the recovery of alkylation are numerous. This is a specific illustration of a more general characteristic of energy utilization, namely that it is usually less difficult to utilize the "high grade" heat in a stream at relatively high temperature than it is to use the "low grade" or waste heat at relatively low temperature.

The "high grade" heat in the reactor effluent of prior art alkylation processes that use SPA catalyst is generally and most conveniently used in one or more rectifiers to separate some of the aromatic feed hydrocarbon from the alkylation reaction effluent for recycle to the alkylation reactor. The alkylation reaction effluent passes to the rectifier, and much of the water, the nonaromatics such as light paraffins, and the aromatic feed hydrocarbon in the alkylation reaction effluent is recovered as a rectifier overhead stream. The rectifier overhead stream is passed to a depropanizer or a deethanizer, which rejects the water and nonaromatics as an overhead stream and recycles to the alkylation zone a bottom stream that is rich in aromatic feed hydrocarbon. In fact, the bottom stream of the depropanizer or deethanizer is usually so dry that water must typically be injected to the alkylation reaction zone in order to maintain the alkylation reaction zone sufficiently wet. The rectifier bottom stream is passed to a fractionation column, often referred to as the recycle column or the benzene column, from which the bulk of the aromatic feed hydrocarbon, together with residual water, is recovered as an overhead stream. The net overhead stream of the recycle column is recycled to the alkylation reactor.

The separation arrangement described in the previous paragraph produces a recycle column net overhead stream which is acceptably dry for recycling to a SPA or zeolitic alkylation catalyst but which without further drying is unacceptably wet for recycling to a zeolitic transalkylation catalyst. Thus, in switching from SPA catalyst to zeolitic catalyst in an existing alkylation process, changes to the alkylation flow scheme should or need to be made. One such change has already been mentioned, namely the addition of a transalkylation reactor, if not already present. Where the transalkylation reactor contains a zeolitic catalyst, however, other changes are necessary in order to produce a recycle column net overhead stream that is sufficiently dry for the zeolitic transalkylation catalyst. Consequently, variations on the separation arrangement for the alkylation reaction effluent that is described in the previous paragraph have been proposed.

One proposed variation would eliminate the rectifier, pass the alkylation reaction effluent directly to the depropanizer or deethanizer, and pass the bottom stream of the depropanizer or deethanizer to the recycle column. The paper entitled "A New Highly Selective Zeolite Catalyst for Cumene Production," written by A. Hernandez-Robinson, et al., and presented at the Worldwide Solid Acid Process Conference in Houston, Tex., on Nov. 14–16, 1993, which describes this proposed variation, is illustrative of the direction taken by the prior art in revamping SPA alkylation processes to zeolitic alkylation processes. The heat in the alkylation reaction effluent of processes that use zeolitic catalysts is "low grade" and generally is insufficient to recover much of the aromatic feed hydrocarbon unless more energy is supplied to the alkylation reaction effluent itself or to the depropanizer or deethanizer. Thus, the alkylation reaction effluent is not passed to a rectifier but instead is passed directly to a depropanizer or deethanizer, and the bottom stream of the depropanizer or deethanizer, which contains essentially all of the aromatic feed hydrocarbon as well as heavier hydrocarbons is then in turn passed to the recycle column. Such a process variation has at least two major disadvantages. First, passing the entire alkylation reaction effluent, rather than a rectified portion of the alkylation reaction effluent, to an existing depropanizer or deethanizer is disadvantageous because it necessitates a costly enlargement or replacement of the existing depropanizer or deethanizer. Second, passing the bottom stream of the depropanizer or deethanizer to the recycle column is disadvantageous because zeolitic catalysts operate at a high ratio of aromatic feed hydrocarbon to alkenes and there is a relatively large abundance of aromatic feed hydrocarbon in the bottom stream of the depropanizer or deethanizer. Passing so much of the aromatic feed hydrocarbon to the recycle column thus necessitates a large-capacity recycle column as well as a large expenditure of utilities to vaporize and lift the aromatic feed hydrocarbon to the top of the recycle column. In addition, because it is common that the aromatic feed hydrocarbon is a liquid when passed to the alkylation reactor, more utilities must then be expended to condense the aromatic feed hydrocarbon in order for it to be recycled from the overhead of the recycle column to the alkylation reactor.

Another proposed variation would eliminate the rectifier, add a few extra trays to the top of the recycle column, and operate the recycle column to withdraw a relatively wet aromatic feed hydrocarbon stream as an overhead stream that is passed to the alkylation reactor and to withdraw a relatively dry aromatic feed hydrocarbon stream as a sidecut that is passed to the transalkylation reactor. U.S. Pat. No. 5,177,285 issued to Van Opdorp et al. discloses this proposed variation. This proposed variation, however, has the undesirable effect of preventing the water content of the sidecut stream of the recycle column from becoming sufficiently dry because of the fact that all of the water that is ultimately removed with the overhead stream of the recycle column must pass through the sidecut tray, thereby contaminating the sidecut stream with water.

Accordingly, methods are sought for producing an aromatic feed hydrocarbon stream for a relatively dry transalkylation reaction zone in a process that uses a relatively wet alkylation reaction zone. In particular, such methods are sought for existing alkylation-transalkylation process units that are being revamped to a higher alkylation reaction zone throughput to convert from using solid phosphoric acid (SPA) transalkylation catalyst, which could tolerate relatively wet transalkylation conditions, to the current zeolitic transalkylation catalysts, which require relatively dry transalkylation conditions.

SUMMARY OF THE INVENTION

This invention is an improved method of separating the alkylation reaction effluent which produces an aromatic feed hydrocarbon stream having a water concentration sufficiently low to be passed to a zeolitic catalyst transalkylation reactor. Instead of passing the alkylation reaction effluent to a rectifier as in the prior art processes, this invention passes the alkylation reaction effluent to a stripper. The stripper bottom stream then passes to the recycle column, and a portion of the recycle column overhead stream passes to the transalkylation reactor. One benefit of using a stripper rather than a rectifier is that enough water can be removed from the alkylation reaction effluent that the recycle column overhead stream is dry enough to be passed directly to the transalkylation reactor. Another benefit of using a stripper is that the stripper also removes aromatic feed hydrocarbon from the alkylation reaction effluent, thereby decreasing the volumetric flow of aromatic feed hydrocarbon that is passed to the recycle column. Thus, the size and capacity of the recycle column can be decreased.

It is well known in the art that a rectifier and a stripper are distinctly different both in their appearance and function. The differences between a rectifier and a stripper are readily apparent by considering distillation processes in general. Distillation processes rely on the well-known tendency that when liquid and vapor phases contact, the more volatile components tend to concentrate more in the vapor phase than in the liquid phase. In single-stage operation, this concentration of the more volatile component in the vapor phase is achieved by partially vaporizing a liquid mixture and then separating the liquid and vapor phases. In multistage operation, a liquid descends a vertical distillation column and passes through a number of stages in which it is contacted counter currently by ascending vapor. The point at which feed is introduced to the distillation column divides the column into two sections. The stripping section is below the feed point, and the rectifying section is above the feed point. In the stripping section, the more volatile component is stripped from the descending liquid. In the rectifying section, the concentration of the less volatile component in the vapor is reduced. In practice, the stages in which the streams of liquid and vapor contact each other may be trays or packing material.

Therefore, a stripper is different in one aspect from a rectifier in that the feed to a stripper is at the top of a number of stages, whereas the feed to a rectifier is at the bottom of a number of stages. In another aspect, a stripper is different from a rectifier in that a stripper strips the more volatile component from the descending liquid, whereas a rectifier reduces the concentration of the less volatile component in the vapor. Thus, a stripper does not function as a rectifier, and where the art teaches the use of a rectifier, a person of ordinary skill in the art would not replace the rectifier with a stripper. Accordingly, a person of ordinary skill views a stripper and a rectifier as two distinct methods of separation.

This invention provides a novel process for removing water and recycle aromatic feed hydrocarbon from the alkylation reaction effluent by passing the alkylation reaction effluent to a stripper. The stripper removes water so that the overhead stream of the recycle column is a dry aromatic feed hydrocarbon stream that is suitable for passing directly to a transalkylation reaction zone that operates at a low water content. The stripper also removes recycle aromatic feed hydrocarbon in order to decrease the quantity of aromatic feed hydrocarbon that is passed to the recycle column, thereby decreasing the cost of building and operating the recycle column. Thus, this invention provides for an efficient and economical use of the "low grade" heat in the alkylation reaction effluent for separating water and recycle aromatic feed hydrocarbon from the alkylation reaction effluent. This invention utilizes the heat of reaction in a more effective manner than the prior art processes that pass the alkylation reaction effluent to a depropanizer or deethanizer.

This invention is an effective method of using the waste heat of the effluent stream of an alkylation reactor effluent, particularly when the temperature of the effluent stream is relatively low. Using a stripper, the waste heat is used to remove water and recycle aromatic feed hydrocarbon from the alkylation reaction effluent. Unlike prior art processes that pass the alkylation reaction effluent to a rectifier, the bottoms stream of the stripper contains a much lower water concentration than the bottom stream of the rectifier. Accordingly, the stripper bottom stream can be directly passed to the recycle column. Consequently, the overhead stream of the recycle column in this invention, but not in the prior art processes, can be passed directly to a transalkylation reaction zone that operates at a low water concentration. Unlike prior art processes that pass the alkylation reaction effluent to a depropanizer or a deethanizer, the bottoms stream of the stripper contains a much lower benzene content than the bottom stream of the depropanizer or deethanizer. As a result, the size of the recycle column, its reboiler, and its overhead condenser are decreased.

The present invention is particularly well-suited for maximizing the use of existing equipment when an existing alkylation process that was originally designed to use solid phosphoric acid (SPA) alkylation catalyst is revamped to use zeolitic catalyst. Because zeolitic catalysts are much more catalytically active than SPA catalysts, changing from SPA catalyst to zeolitic catalyst in an existing process provides an ideal opportunity to significantly increase the alkylation reaction zone throughput of the process typically by 150 to 200 percent. However, prior art revamps of existing alkylation processes have not made efficient use of the existing equipment and are, therefore, unnecessarily costly. For example, an existing process typically has one or two existing rectifiers that were designed to be fed a vapor-phase alkylation reaction effluent and to flash aromatic feed hydrocarbon. Prior art revamps have not used the existing rectifiers in the revamped process especially where the alkylation reaction effluent is liquid-phase, because persons of ordinary skill in the art have deemed the rectifiers as unsuitable. In addition, an existing process also typically has a recycle column that was designed to provide the recycle requirements of aromatic feed hydrocarbon to the SPA alkylation reactor alone. Prior art revamps in which the increase in alkylation reaction zone throughput is substantial have required either complete replacement of the existing recycle column or construction of a new recycle column in parallel with the existing recycle column. Such costly revamps have been made in order to augment the existing recycle column where the recycle column must provide the recycle requirements of aromatic feed hydrocarbon to not only the zeolitic alkylation reactor but also the zeolitic transalkylation reactor, because persons of ordinary skill in the art have deemed the existing recycle column as too small.

This invention is in one aspect a novel and particularly effective method of using the existing rectifier(s) and the existing recycle column of a SPA catalyst process following the revamp to a zeolitic catalyst process in which the alkylation reaction zone throughput is increased significantly. By moving the feed point of an existing rectifier from below the bottom tray to a point above the top tray and by adding a reboiler, the existing rectifier may be used as a stripper for removing water from the alkylation reaction effluent. In addition, by introducing the feed to above the top tray of the rectifier-turned-stripper, a portion of the aromatic feed hydrocarbon is removed from the alkylation reaction effluent as well. Removing aromatic feed hydrocarbon from the overhead rather than from the bottom of the stripper decreases the quantity of aromatic feed hydrocarbon that is passed to the recycle column. This in turn allows the existing recycle column of a SPA catalyst process to be used as the recycle column in a zeolitic catalyst process, even though the alkylation reaction zone throughput has been increased significantly. Thus, in practicing this aspect of the invention, the revamp of an existing SPA catalyst process to a zeolitic catalyst process may be done in a manner that maximizes the use of the existing equipment and minimizes the costs of revamping to a zeolitic catalyst process in spite of a significant increase in alkylation reaction zone throughput.

Accordingly, in a broad embodiment, this invention is a process for the production of alkylaromatic hydrocarbons. An aromatic feed hydrocarbon and an acyclic feed hydrocarbon are contacted with an alkylation catalyst in an alkylation zone at alkylation conditions. The aromatic feed hydrocarbon is reacted in the alkylation zone with the acyclic feed hydrocarbon to produce an aromatic product hydrocarbon. An alkylation reaction zone effluent comprising the aromatic feed hydrocarbon, the aromatic product hydrocarbon, polyalkylated aromatic hydrocarbons, and water is recovered from the alkylation zone. The alkylation reaction zone effluent is passed to a stripping column wherein water is removed from the alkylation reaction zone effluent. A stripped alkylation reaction zone effluent is withdrawn as a bottom stream of the stripping column. The stripped alkylation reaction zone effluent comprises the aromatic feed hydrocarbon, the aromatic product hydrocarbon, and the polyalkylated aromatic hydrocarbon, and has a water concentration that is less than the water concentration of the alkylation reaction zone effluent. The stripped alkylation reaction zone effluent and a transalkylation reaction zone effluent comprising the aromatic product hydrocarbon are passed to a separation zone. The hydrocarbons are separated in the separation zone into an alkylate stream comprising the aromatic product hydrocarbon and the polyalkylated aromatic hydrocarbon and a first recycle stream comprising the aromatic feed hydrocarbon. The alkylate stream and the first recycle stream are withdrawn from the separation zone. The alkylate stream is separated into a second recycle stream comprising the polyalkylated aromatic hydrocarbon and a product stream comprising the aromatic product hydrocarbon. At least a portion of the first recycle stream and at least a portion of the second recycle stream is passed to a transalkylation zone containing a transalkylation catalyst at transalkylation conditions. The transalkylation conditions comprise a water concentration of less than the water concentration of the alkylation conditions. In the transalkylation zone, the aromatic feed hydrocarbon is reacted with the polyalkylated aromatic hydrocarbon to produce the aromatic product hydrocarbon. The transalkylation reaction zone effluent is recovered from the transalkylation zone.

In another embodiment, this invention is a process for the production of cumene. A benzene feed and a propylene feed are contacted with an alkylation catalyst comprising beta zeolite in an alkylation zone at alkylation conditions. The alkylation conditions comprise a liquid phase, a temperature of from 302° to 518° F., a pressure of from 150 to 2000 psi(g), and a water concentration of at least 30 wppm. In the alkylation zone, benzene and propylene are reacted to produce cumene. An alkylation reaction zone effluent comprising benzene, cumene, diisopropylbenzene, heavier alkylated aromatic hydrocarbons, and water is recovered from the alkylation zone. The alkylation reaction zone effluent is passed to a stripping column. Water is removed from the alkylation reaction zone effluent in the stripping column. A stripped alkylation reaction zone effluent is withdrawn as a bottom stream of the stripping column. The stripped alkylation reaction zone effluent comprises benzene, cumene, diisopropylbenzene, and the heavier alkylated aromatic hydrocarbons, and contains less than 10 mol-% of the water and less than 73 mol-% of the benzene in the alkylation reaction zone effluent. The stripped alkylation reaction zone effluent and a transalkylation reaction zone effluent comprising cumene are passed to a first fractionation column. The hydrocarbons are separated in the first fractionation column into an alkylate stream comprising cumene, diisopropylbenzene, and the heavier alkylated aromatic hydrocarbons, and a first recycle stream comprising benzene. The alkylate stream and the first recycle stream are withdrawn from the first fractionation column. At least a portion of the first recycle stream is passed to the alkylation zone. The alkylate stream is passed to a second fractionation column, and the hydrocarbons are separated in the second fractionation column into an intermediate separation stream comprising the diisopropylbenzene and the heavier aromatic hydrocarbons and a product stream comprising cumene. The intermediate separation stream and the product stream are withdrawn from the second fractionation column. The intermediate separation stream is passed to a third fractionation column. In the third fractionation column, the hydrocarbons are separated into a second recycle stream comprising diisopropylbenzene and a heavy aromatic stream comprising the heavier alkylated aromatic hydrocarbons. The second recycle stream and the heavy aromatic stream are withdrawn from the third fractionation column. At least a portion of the first recycle stream and at least a portion of the second recycle stream are passed to a transalkylation zone containing a transalkylation catalyst comprising beta zeolite at transalkylation conditions. The transalkylation conditions comprise a temperature of from 392° to 500° F., a pressure of from 150 to 2000 psi(g), and a water concentration of less than 20 wppm. In the transalkylation zone benzene and diisopropylbenzene react to produce cumene. The transalkylation reaction zone effluent is recovered from the transalkylation zone.

INFORMATION DISCLOSURE

U.S. Pat. No. 5,177,285 issued to Van Opdorp et al. discloses an aromatic alkylation process for producing ethylbenzene in which a high water content in an alkylation zone and a low water content in a transalkylation zone are maintained by using a separation zone that removes water from a benzene sidecut. The teachings of U.S. Pat. No. 5,177,285 are incorporated herein by reference.

U.S. Pat. No. 5,336,821 issued to DeGraff et al. discloses an aromatic alkylation process that uses zeolite beta.

U.S. Pat. No. 5,030,786 discloses an alkylation process wherein the feedstream is dehydrated to enhance the performance of beta zeolite in the alkylation process.

U.S. Pat. No. 4,695,665 issued to DeGraff discloses an alkylation process wherein the alkylation reaction effluent is passed to a lower portion of a rectified separation zone.

U.S. Pat. No. 4,051,191 issued to Ward discloses a typical flow scheme for the commercial production of cumene in which the reactor effluent is passed to a rectification zone, and the liquid phase hydrocarbons from the rectification zone are passed to a two-column fractionation train for recycle of benzene and recovery of cumene.

U.S. Pat. No. 3,520,945 issued to DeGraff discloses an alkylation process that controls the water content of the alkylation catalyst by saturating a portion of the feedstream and passing the saturated feedstream to a rectification zone.

U.S. Pat. No. 2,787,648 discloses a SPA catalyst alkylation process wherein the alkylation reaction effluent is passed, after removal of phosphoric acid, to a depropanizer having a stripping section and a rectification section.

A paper entitled "Catalytic Distillation Route for Cumene," written by A. Sly, et al., and presented at the Dewitt Petrochemical Review in Houston, Tex., on Mar. 23–25, 1993, shows at pages Q-14 and Q-21 an alkylation-transalkylation process for cumene that employs a catalytic distillation column having a reactor section and a distillation section.

A paper entitled "A New Highly Selective Zeolite Technology for Cumene," written by A. Hernandez-Robinson, et al., and presented at the Dewitt Petrochemical Review in Houston, Tex. on Mar. 23–25, 1993, discloses a zeolitic alkylation-transalkylation process for cumene.

A paper entitled "A New Highly Selective Zeolite Catalyst for Cumene Production," written by A. Hernandez-Robinson, et al., and presented at the Worldwide Solid Acid Process Conference in Houston, Tex., on Nov. 14–16, 1993, discloses a zeolitic alkylation-transalkylation process for cumene where the alkylation reaction effluent is passed to a depropanizer.

BRIEF DESCRIPTION OF THE DRAWING

The drawing is a schematic illustration of an alkylation-transalkylation process with a stripping column arranged in accordance with this invention.

DETAILED DESCRIPTION OF THE INVENTION

This invention is suitable for a wide variety of feedstocks. Suitable aromatic feed hydrocarbons for this invention include various aromatic substrates. Such substrates can be alkylated aromatic hydrocarbons such as alkyl substituted benzenes but are preferably unsubstituted benzenes. The acyclic feed hydrocarbon or alkylating agent that may be used in the alkylation reaction zone also encompasses a broad range of hydrocarbons. Suitable alkylating agents include monoolefins, diolefins, polyolefins, acetylenic hydrocarbons and other substituted hydrocarbons but are preferably $C_2$–$C_4$ hydrocarbons. In the most preferred form of this invention, the alkylation agent will comprise $C_2$–$C_4$ monoolefins, including ethylene and propylene.

A catalyst promotes the initial alkylation in the alkylation reaction zone. A wide variety of catalysts can be used in the alkylation reaction zone. Suitable catalysts for use in the reaction zone will comprise any catalyst that does not suffer deleterious effects from the presence of water. Preferably, but not necessarily, a substantial quantity of water will enhance the performance of the alkylation catalyst. The preferred catalyst for use in this invention is a zeolitic catalyst. The zeolitic molecular sieves suitable for use in the present invention are crystalline aluminosilicates which in the calcined form may be represented by the general formula:

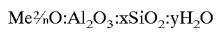

$$Me_{2/n}O:Al_2O_3:xSiO_2:yH_2O$$

where Me is a cation, n is the valence of the cation, x has a value of from about 5 to 100, and y has a value of from about 2 to 10. Detailed descriptions of zeolites may be found in D. W. Breck, *Zeolite Molecular Sieves*, John Wiley and Sons, New York 1974, and in other standard references. A preferred zeolite is zeolite beta as disclosed in U.S. Pat. Nos. 4,891,458 and 5,081,323, the teachings of which are incorporated herein by reference. It is believed that mordenite and zeolite omega can also be suitable catalysts for this invention. The zeolite will usually be used in combination with a refractory inorganic oxide binder. Preferred binders are alumina or silica. Suitable alkylation catalysts are a type Y zeolite having an alumina or silica binder or a beta zeolite having a silica binder. The preferred alkylation catalyst is beta zeolite having an alumina binder. The zeolite will preferably be present in an amount of from 10 to 90 wt-% of the catalyst and more preferably in an amount of from 70 to 80 wt-% of the catalyst.

The alkylation reaction zone can operate under a broad range of operating conditions. Temperatures usually range from 194° to 518° F. (90° to 270° C.), with from 194° to 356° F. (90° to 180° C.) preferred for producing cumene and from 302° to 518° F. (150° to 270° C.) preferred for producing ethylbenzene. Pressures can also vary within a wide range of from 150 to 2000 psi(g) (1030 to 13790 kPa(g)). Since liquid phase conditions are generally preferred within the reaction zone, the pressure should be sufficient to maintain the reactants in such phase and will typically fall within a range of from 450 to 650 psi(g) (3103 to 4482 kPa(g)). Reactants generally pass through the alkylation zone at a mass flow rate sufficient to yield an olefin liquid hourly space velocity from 0.2 to 50 hr$^{-1}$ and preferably from 0.5 to 3 hr$^{-1}$. The water concentration in the alkylation reactor can generally be from nil to the saturation concentration of water in the reactants at the alkylation conditions, and preferably from 30 to 300 wppm.

The alkylation zone is ordinarily operated to obtain an essentially complete conversion of the alkylating agent to monoalkylate and polyalkylate. To achieve this effect, additional aromatic feed hydrocarbon will usually be charged to the alkylation reaction zone. As a result, in addition to the aromatic product hydrocarbon there will usually be a substantial amount of unreacted aromatic feed hydrocarbon that is removed with the alkylation effluent stream from the alkylation reaction zone. For this reason, the molar ratio of aromatic feed hydrocarbon to alkylation agent in the alkylation feed stream is often a useful operating variable.

An even more useful operating variable for the alkylation reaction zone, however, is the molar ratio of phenyl group per alkyl group of the alkylation reactants. For producing cumene the molar ratio of phenyl group per propyl group is preferably from 3:1 to 4:1, and for producing ethylbenzene the molar ratio of phenyl group per ethyl group is preferably about 6:1. The moles of phenyl groups is the sum of the moles of phenyl groups of aromatic feed hydrocarbon plus the moles of phenyl groups of other aromatic hydrocarbons. In this context, the term "other aromatic hydrocarbons" includes the aromatic product hydrocarbon as well as aromatic by-product hydrocarbons such as polyalkylated aromatic hydrocarbons. Thus, for example, one mole of benzene, one mole of cumene (isopropylbenzene), and one mole of diisopropylbenzene each contribute one mole of phenyl group to the sum of the phenyl groups in the reactants. The moles of alkyl groups is the sum of the moles of alkyl groups of the aromatic feed hydrocarbon, the moles of alkylation agents, the moles of alkyl groups of the aromatic product hydrocarbon, and the moles of alkyl groups of other alkylated aromatic hydrocarbons. In this context, the term "other alkylated aromatic hydrocarbons" includes aromatic by-product hydrocarbons such as polyalkylated aromatic hydrocarbons. Accordingly, for example, one mole of ethylene and one mole of ethylbenzene each contribute one mole of alkyl group to the sum of alkyl groups in the reactants, whereas one mole of diethylbenzene contributes two moles of alkyl groups.

As mentioned, the alkylation reaction zone will often provide a wide variety of undesired by-products. For example, in the alkylation of benzene with propylene to produce cumene, the alkylation reaction zone can also produce di- and tri-propylbenzene in addition to other propylene condensation by-products. The transalkylation arrangement of this invention transalkylates the polyalkylated aromatic by-products in the presence of additional aromatic feed hydrocarbon to yield additional monoalkylated aromatic products. Therefore, a number of separation stages are needed to separate the monoalkylated aromatic product from the other by-products.

This invention, in one aspect, provides a modification to the common arrangements of rectification columns and separators that separate the alkylation reaction effluent and supply an aromatic feed hydrocarbon stream that has a low water concentration. By passing the alkylation reaction effluent into a stripping column rather than into a rectification column, enough water can be removed to decrease the concentration of water in the transalkylation reaction zone to less than the concentration of water in the alkylation reaction zone, in particular to preferably less than 100 wppm and more preferably to less than 20 wppm. The modification from a rectification column to a stripping column is particularly straightforward for an existing alkylation process with an existing rectification column. Again, in the context of cumene and ethylbenzene production, the modification of an existing rectification column to achieve the desired degree of drying will typically involve moving the feed point from a point below the bottom-most tray of the rectification column to a point above the top-most tray of the rectification column. Moreover, the number of existing trays in an existing rectification column, namely from 4 to 10 trays, is generally also the desired number of trays for the stripping column. If the type or style of the existing rectification trays are not suitable for stripping, then the existing rectification column is used and simply the existing trays are replaced. If, however, the number of rectification trays is not adequate to achieve the desired degree of stripping, then the addition of a few extra trays to the rectification column, or replacement of the existing trays with more-efficient contacting material such as packing, will be sufficient to accomplish the desired degree of drying for stripping. It is much easier and less expensive to add a few extra trays or to add packing to a rectification column than it is to follow the teachings of U.S. Pat. No. 5,177,285 and to add extra trays to a benzene column, which is generally much bigger in diameter and in length than a rectification column. Where the alkylation reaction effluent is liquid-phase, a reboiler must be added to the bottom of the stripping column in order to achieve the desired degree of drying. In sum, the modification of an existing rectification column to allow it to be used as a stripping column is a particularly advantageous and economical method of implementing this invention in an existing alkylation process.

The stripping column can operate under a broad range of operating conditions. In general, because stripping water from the alkylation reaction effluent tends to strip aromatic product hydrocarbon from the alkylation reaction effluent also, the desired degree of stripping depends in part on the desired degree of recovery of aromatic product hydrocarbon in the stripper bottoms stream, that is in the stripped alkylation reaction effluent. Stripping bottom temperatures usually range from 400° to 450° F. (205° to 232° C.), with 410° to 415° F. (210° to 213°° C.) being preferred. Overhead temperatures usually range from 340° to 400° F. (171° to 204° C.), with 360° to 365° F. (182° to 185° C.) being preferred. Pressures can vary from 200 to 250 psi(g) (1379 to 1724 kPa(g)). Where an existing rectification column is being converted to a stripping column, operating conditions for stripping can generally be optimized in a manner so that the conditions are within the design conditions of the existing rectification column.

The stripping column separates the alkylation reaction effluent stream into a stripping overhead stream and a stripping bottoms stream. The stripping overhead stream generally comprises water, nonaromatics, the aromatic feed hydrocarbon, and some aromatic product hydrocarbon. The stripping column overhead stream generally removes at least 90 mol-%, and preferably at least 96 mol-%, of the water in the alkylation reaction effluent so that the stripping bottoms stream contains less than 10 mol-%, and preferably less than 4 mol-%, of the water in the alkylation reaction effluent. The stripping column bottom stream contains generally less than 50 wppm.water and preferably less than 20 wppm water. The nonaromatics in the stripping column overhead stream include nonaromatics that entered the process in the stream containing the alkylating agent. These nonaromatics can include paraffins such as $C_2$–$C_4$ paraffins, nitrogen, and carbon dioxide. In a cumene process, propane is generally present in the alkylation reaction effluent and generally at least 99.0 mol-%, and preferably at least 99.9 mol-%, of the propane is removed from the alkylation reaction effluent by the stripping column. Thus, the stripping bottoms stream contains less than 1 mol-%, and preferably less than 0.1 mol-%, of the propane in the alkylation reaction effluent. In an ethylbenzene process, ethane rather than propane is generally present in the alkylation reaction effluent, and accordingly the desired extent of removal of ethane is the same as that for propane in a cumene process. Unconverted monoolefins are present, if at all, at concentrations of less than 0.5 mol-%, because the relatively high ratio of aromatic feed hydrocarbon to alkylating agent results in monoolefin conversion of more than 99.0%

The stripping column also removes aromatic feed hydrocarbon from the alkylation reaction effluent. This is beneficial because the greater the removal of the aromatic feed hydrocarbon by the stripping column, the greater is the amount of aromatic feed hydrocarbon that can be recycled to the alkylation reactor without being passed to the recycle column. This in turn decreases the cost of building and operating the recycle column or debottlenecks the recycle column. As mentioned previously, the stripping column generally removes water from the alkylation reaction effluent. However, if the alkylation conditions are dry and the water content of the alkylation reaction effluent is less than about 30 wppm, then it may not be necessary for the stripping column to remove water in order to maintain sufficiently dry transalkylation conditions. In that case, the stripping column would preferably be operated to remove a sufficient portion of the aromatic feed hydrocarbon from the alkylation reaction effluent. Accordingly, the stripping column generally removes at least 20 mol-%, and preferably at least 27 mol-%, of the aromatic feed hydrocarbon in the alkylation reaction effluent, and thus the stripping bottoms stream contains less than 80 mol-%, and preferably less than 73 mol-%, of the aromatic feed hydrocarbon in the alkylation reaction effluent. On the other hand, removal of the aromatic product hydrocarbon by the stripping column is generally not preferred, because any aromatic product hydrocarbon that is present in the stripping column overhead stream represents valuable product which, rather than being passed on to the recycle column and ultimately recovered in the product column, is instead recycled to the alkylation reactor. Thus, the presence of aromatic product hydrocarbon in the net overhead stream of the stripping column is preferably minimized. Accordingly, the stripping column overhead stream generally contains less than 20 mol-%, and preferably less than 10 mol-%, and more preferably less than 5 mol-%, of the aromatic product hydrocarbon in the alkylation reaction effluent.

Optionally, a rectification section may be used in conjunction with the stripping column, with the overhead stream of the stripping section in effect being passed to a rectification section. In practice, this rectification section may be added above the stripping column by installing several contacting trays or packing above the feed point of the stripping column and by injecting reflux above the upper-most tray or the packing. The rectification section need not, however, be contained in the same column with the stripping section. For example, the rectification section may be a single-stage contactor for contacting the stripping column overhead vapor stream and a liquid reflux stream. The liquid stream from the rectification section can be passed to the stripping column. The addition of a rectification section increases the aromatic feed hydrocarbon content of the stripping vapors in the stripping column while minimizing the amount of aromatic product hydrocarbon that is not recovered in the stripping column bottom stream. The reflux stream for the rectification section may be a condensed portion of the rectification section overhead stream. Alternatively, the reflux may be a portion of the fresh aromatic feed hydrocarbon, a portion of the depropanizer bottom stream, or a portion of the recycle column overhead stream. Although in general it may not be necessary to add the rectification section, when converting an existing SPA catalyst process to a zeolitic catalyst process the use of a rectification section can lead to substantial cost savings by further debottlenecking an existing recycle column. Thus, unlike the prior art revamps, the use of a rectification section in conjunction with the stripping column can preclude the need to replace or augment the existing recycle column.

When a rectification section is not used in conjunction with the stripping column, the stripping column overhead stream is preferably passed without condensation to a column that separates the stripping column overhead stream into an overhead stream containing water and nonaromatics and a bottom stream containing aromatic feed hydrocarbon and monoalkylated aromatic hydrocarbon product. When a rectification section is used in conjunction with the stripping column, the stripping column overhead stream is preferably passed to this column. In the context of cumene production this column is usually a depropanizer and in the context of ethylbenzene production this column is usually a deethanizer. Where this invention is applied to an existing cumene or ethylbenzene process unit that has an existing depropanizer or deethanizer respectively, that existing column, including its design conditions, are generally suitable with little or no modifications for separating the stripping column overhead stream, unless the process unit is being revamped for a significant increase in alkylation reaction zone throughput. In the case of cumene production, the depropanizer column can operate under a broad range of operating conditions. For a non-reboiled depropanizer, bottom temperatures usually range from 300° to 375° F. (149° to 191° C.), with 345° to 350° F. (174° to 177° C.) being preferred. Higher bottom temperatures will generally be required for depropanizers with a reboiler and, hence, a stripping section. Overhead temperatures usually range from 102° to 115° F. (39° to 46° C.), with 105° to 110° F. (41° to 43° C.) being preferred. Pressures can vary from 200 to 250 psi(g) (1379 to 1724 kPa(g)).

The overhead stream of the depropanizer or deethanizer usually contains from 0.10 to 0.15 mol-% water and from 95 to 99 mol-% nonaromatics, such as $C_2$–$C_4$ paraffins, nitrogen, and carbon dioxide. It is preferable to operate the depropanizer or deethanizer in order to minimize the amount of aromatic feed hydrocarbon or aromatic product hydrocarbon in the overhead stream. The overhead stream of the depropanizer or deethanizer is usually at least partially condensed and passed to an overhead receiver, and a portion of the condensed overhead stream is usually returned to the stripping column as reflux. Usually, a water-rich portion of the condensed overhead stream is withdrawn from the overhead receiver in order to prevent water from accumulating in the overhead of the depropanizer or deethanizer. A separate portion of the condensed overhead stream that is not water-rich and that comprises the remaining nonaromatics is withdrawn separately from the overhead receiver and is also rejected from the process. As used herein, a stream that is "rich" in a component is a stream that contains more than 50 mol-% of that component. Optionally, the net overhead nonaromatics stream from the depropanizer or deethanizer may be withdrawn as a vapor stream from a point upstream of the overhead condenser.

The bottom stream of the depropanizer or deethanizer generally contains from 10 to 300 wppm water, from 65 to 95 mol-% aromatic feed hydrocarbon, and from 1 to 5 mol-% aromatic product hydrocarbon. Depending on the concentrations of water and aromatic product hydrocarbon in the bottom stream of the depropanizer or deethanizer, the bottom stream either can be passed to the alkylation reaction zone or can be passed to the recycle column and from there to the transalkylation reaction zone, both of which are described hereinafter. In those cases where the depropanizer or deethanizer has no stripping section below the feed point, the bottom stream of the depropanizer or deethanizer will have a relatively high water content. In such a case, the bottom stream is generally passed to the alkylation reaction zone, because the amounts of either water or aromatic product hydrocarbon that are passed to the alkylation catalyst in such a case usually do not have a significant adverse effect on the performance of the alkylation catalyst. In those cases where the depropanizer or deethanizer has a stripping section below the feed point, the bottom stream of the depropanizer or deethanizer may have a sufficiently low water content so that the bottom stream can be passed to the transalkylation reaction zone. The concentrations of water and aromatic product hydrocarbon which can lead to adverse effects in the alkylation reaction zone and in the transalkylation reaction zone depend on the catalyst and on the operating conditions. It is within the skill of a person of ordinary skill in the art to determine the concentrations of water and aromatic product hydrocarbon at which undesirable effects occur for a particular catalyst and at particular operating conditions.

The stripping column bottom stream, and perhaps the bottom stream of the depropanizer or deethanizer, is passed to the recycle column. In the case of cumene and ethylbenzene production, the recycle column is generally referred to as the benzene column. The transalkylation reaction effluent, which is described hereinafter, is also passed to the recycle column. Thus, the streams that are fed to the recycle column generally contain feed aromatic hydrocarbon, aromatic product hydrocarbon, heavier alkylated aromatics, and residual water. The recycle column separates these components into an overhead stream comprising the feed aromatic hydrocarbon and residual water and a bottom stream which contains the higher boiling reaction products. Essentially all of the water that enters the recycle column exits in the net overhead stream of the recycle column. Because a portion of the net overhead stream is fed to the transalkylation reactor, and because it is an object of this invention to decrease the water concentration of the transalkylation conditions, the water content of the recycle column overhead stream is generally less than 500 wppm, and preferably is less than 20 wppm.

Alternatively, the stripping column bottom stream can be passed to a rectification column and the bottom stream of the rectification column comprising aromatic product hydrocarbon and heavier alkylated aromatics can then be passed to the recycle column. The overhead of the rectification column comprises aromatic feed hydrocarbon and can be passed to the alkylation reaction zone or to the transalkylation reaction zone. Reflux for the rectification column can be a condensed portion of the rectification column overhead stream or a condensed portion of the recycle column overhead stream. This alternative arrangement removes even more of the aromatic feed hydrocarbon from the feed to the recycle column, thereby further debottlenecking the recycle column. This alternative arrangement is particularly applicable in the conversion to a zeolitic process of an existing SPA catalyst process that has two rectifiers. In such a case, one rectifier can be converted to a stripping column and the second rectifier can be used as the rectification column to which the stripping column bottom stream is passed.

The bottom stream of the recycle column, which contains the aromatic product hydrocarbon and the heavier alkylated aromatic hydrocarbons, is passed to the product column. The product column is generally referred to in cumene processes as the cumene column and in ethylbenzene processes as the ethylbenzene column. The net overhead stream of the product column contains the product aromatic hydrocarbon, which is recovered as the product of the process. The net bottom stream of the product column is passed to a heavy aromatic hydrocarbon column. The heavy aromatic hydrocarbon column separates a particular group of heavy aromatic hydrocarbons, namely those compounds that consist of the aromatic feed hydrocarbon alkylated by two alkylation agents, from the remainder of the heavy aromatic hydrocarbons. In the case of cumene production this particular group of hydrocarbons comprises the diisopropylbenzenes, whereas in ethylbenzene production this group of hydrocarbons comprises the diethylbenzenes. A stream comprising is recovered from the heavy aromatic hydrocarbon column and is recycled to the transalkylation reaction zone. The other heavy aromatic hydrocarbons are rejected by the heavy aromatic hydrocarbon column from the process.

As described previously, the alkylation reaction zone produces polyalkylated aromatic compounds as well as the desired monoalkylated aromatic product. These polyalkylated aromatics contact additional aromatic feed hydrocarbon in a transalkylation reactor to redistribute alkyl groups and produce additional monoalkylated product. The transalkylation reaction zone of this invention will preferably use a zeolitic catalyst. The zeolitic molecular sieves suitable for use in the present invention are crystalline aluminosilicates which in the calcined form may be represented by the general formula:

where Me is a cation, n is the valence of the cation, x has a value of from about 5 to 100, and y has a value of from about 2 to 10. A preferred zeolite is zeolite beta as disclosed in U.S. Pat. Nos. 4,891,458 and 5,081,323. It is believed that mordenite and zeolite omega can also be suitable catalysts for this invention. In most cases the zeolitic catalyst includes an inorganic oxide binder. The preferred inorganic oxide for use in the transalkylation catalyst is alumina with gamma-alumina, eta-aluminum and mixtures thereof being particularly preferred. Suitable transalkylation catalysts are a type Y zeolite having an alumina or silica binder or a beta zeolite having a silica binder. The preferred transalkylation catalyst is beta zeolite having an alumina binder. The zeolite will preferably be present in an amount of from 10 to 90 wt-% of the catalyst and more preferably in an amount of from 70 to 80 wt-% of the catalyst.

Water has been found to have a deleterious effect on the zeolitic catalyst as described previously, and prolonged contact with high concentrations of water will cause the catalyst to lose activity. In order to sustain adequate conversion from the transalkylation zone over a normal run period, the loss in activity is compensated by increasing severity of operation within the reaction zone. The increase in severity causes the transalkylation reactor to lose selectivity and ultimately results in a shortened length of run for the catalyst, a loss in product yields, or combination of the two. By operating the transalkylation reaction zone at a much lower water concentration than alkylation reaction zone, typically a water concentration of less than 100 wppm, no appreciable loss of activity is seen over a reasonable length of run for the process. The water concentration in the transalkylation reaction zone is preferably kept at very low levels of less than 20 wppm. However, prior art processes for maintaining very low water concentrations in the transalkylation zone even at less than 75 wppm require expensive dehydrating equipment that raise the expense of the transalkylation zone. By contrast, this invention provides a simple, efficient, and cost-effective method of maintaining the water concentration in the transalkylation reaction zone at less than 100 wppm and preferably less than 20 wppm.

There is no requirement that the alkylation reaction zone and the transalkylation reaction zone use the same catalyst. This process is useful for any arrangement of alkylation reaction zone and transalkylation reaction zone wherein the operation of the former is benefited by a high water concentration and a high water concentration in the latter is detrimental. However, it has been found that the preferred catalyst for this invention, a beta zeolite catalyst in an alumina binder will perform very well when used in both the alkylation reaction zone and the transalkylation reaction zone. Therefore, in the preferred embodiment of this invention, both reaction zones will use the same catalyst.

The transalkylation reaction can be carried out in a broad range of operating conditions. Temperatures usually range from 284° to 500° F. (140° to 260° C.), with from 284° to 392° F. (140° to 200° C.) preferred for producing cumene and from 392° to 500° F. (200° to 260° C.) preferred for producing ethylbenzene. As with alkylation, generally the pressure is selected so that the reactants remain in the liquid phase. Accordingly, pressures can also vary within a wide range, generally from 150 to 2000 psi(g) (1030 to 13790 kPa(g)), but typically from 450 to 650 psi(g) (3103 to 4482 kPa(g)). Reactants generally pass through the transalkylation zone at a mass flow rate sufficient to yield an total liquid hourly space velocity from 0.2 to 50 $hr^{-1}$ and preferably from 1 to 5 $hr^{-1}$. As already described, the water concentration in the transalkylation reactor is generally less than 100 wppm and preferably less than 20 wppm. For producing cumene by transalkylation the molar ratio of phenyl group per propyl group is preferably from 2:1 to 3:1, and for producing ethylbenzene by transalkylation the molar ratio of phenyl group per ethyl group is preferably from 5:1 to 7:1.

The drawing illustrates a preferred embodiment of the invention. For clarity and simplicity, some items associated with the operation of the process have not been shown. These items include flow and pressure control valves, pumps, heat exchangers, temperature and pressure monitoring systems, reactor and fractionator internals, etc., which may be of customary design. Such representation of these embodiments is not intended to limit the scope of the present invention as set forth in the claims.

Referring now to the drawing, a stream comprising propylene and nonaromatics such as propane enters the process in a line 12 and is admixed with a stream flowing through a line 14 that comprises benzene and water, thereby producing a first alkylation reactor feed stream carried by a line 16. Water is injected into the process in a line 10. Thus, the first alkylation reactor feed stream flowing through line 16 contains propylene, benzene, cumene, and water. The first alkylation reactor feed stream in line 16 may be heated in a heat exchanger or a heater, which is not shown, and enters a first alkylation reactor 20. The first alkylation reactor feed stream contacts a beta zeolite catalyst maintained at alkylation conditions to alkylate benzene with at least a portion of the propylene to form cumene (isopropylbenzene). Other alkylation reactions involving cumene and propylene can also occur, thereby forming by-products such as methylpropylbenzene, butylbenzene, diisopropylbenzene (DIPB), and heavier alkylated aromatics. The first alkylation reactor effluent stream contains benzene, cumene, DIPB, heavier alkylated aromatics, and water. The first alkylation reactor effluent stream exits the first alkylation reactor 20 in a line 18.

The first alkylation reactor effluent stream enters a heat exchanger 22, where the first alkylation reactor effluent stream is cooled by exchanging heat indirectly with another stream in the process or with boiler feed water to produce low pressure steam. The cooled first alkylation reactor effluent stream passes through a line 24 and is admixed with another stream containing propylene and propane that enters the process in a line 28. This produces a second alkylation reactor feed stream carried by a line 26. The second alkylation reactor feed stream may be heated in a heat exchanger or a heater, which is not shown, and enters a second alkylation reactor 30. The second alkylation reactor feed stream contacts a beta zeolite catalyst maintained at alkylation conditions to alkylate benzene with propylene to produce cumene. The second alkylation reactor effluent stream, which contains benzene, cumene, DIPB, heavier alkylated hydrocarbons, and water, exits the second alkylation reactor 30 in a line 32. The second alkylation reactor effluent stream may be depressured by passing through a pressure control valve which is not shown, may be heated in a heater or heat exchanger which is also not shown, or both. The second alkylation reactor effluent stream then enters a stripping column 40 at a feed point above the top tray of the stripping column 40.

The stripping column 40 separates the second alkylation reactor effluent stream by distillation into two streams. Stripping column 40 is a true stripping column in that it has no fractionation media above the feed point to the stripping column. In addition, stripping column 40 uses no external reflux. The stripping column overhead vapor stream contains benzene, cumene, propane, and water. The stripping column overhead stream exits the stripping column 40 in a line 34 and passes to a depropanizer 50. The stripping column liquid bottom stream contains benzene, cumene, DIPB, and heavier alkylated aromatics and exits in a line 36. A portion of the stripping column bottom stream passes through a line 35, passes through reboiler 37 wherein at least a portion of the benzene is vaporized, and returns to the stripping column 40 through the line 39. The required duty of the reboiler 37 can be decreased somewhat by vaporizing at least a portion of the benzene in the stripping column feed by, as described previously, heating the alkylation reaction effluent in line 32. Another portion of the stripping column bottom stream passes through a line 68 to a separation zone, which is shown in the drawing as a recycle column 70.

As described, the stripping column overhead stream exits the stripping column 40 in a line 34 and passes to a depropanizer 50. Make-up benzene that contains water enters the process in a line 45 and also passes to depropanizer 50. The depropanizer 50 separates the stripping column overhead stream and the make-up benzene by distillation and removes water and nonaromatics such as propane in an overhead vapor stream. The depropanizer overhead vapor stream flows through a line 54, through a condenser 56, through a line 57, and into an overhead receiver 60. A propane-rich liquid stream is withdrawn from the overhead receiver 60 in a line 62. One portion of the overhead liquid stream in line 62 is refluxed to the depropanizer 50 in a line 64, and another portion is rejected from the process through a line 66. Water is withdrawn separately from the overhead receiver 60 in a line 63 and is also rejected from the process. The depropanizer bottom liquid stream from depropanizer 50 comprises benzene, cumene, and water and flows through a line 42. A portion of the bottom liquid stream passes through a line 46, is reboiled in reboiler 48, and returns to the depropanizer 50 through the line 52. Another portion of the bottom liquid stream in line 42 passes through the line 44 and admixes with the stream in line 108 and is recycled to the first alkylation reactor 20 through lines 109, 14, and 16.

Two streams feed the recycle column 70: the portion of the stripping column bottom stream that passes through line 68 as described previously, and the transalkylation reaction effluent in line 88. Preferably the transalkylation reaction effluent enters the recycle column 70 at a point higher in the column than the portion of the stripping column bottom stream. These two streams together pass benzene, cumene, DIPB, heavier alkyl aromatics and residual water to the recycle column 70. A recycle column overhead vapor stream comprising benzene and water exits the recycle column 70 in a line 74, is condensed in condenser 76, and passes through line 78 to overhead receiver 80. A recycle column overhead liquid stream, which is withdrawn from overhead receiver 80 in a line 82, can be routed to four different locations. One portion of the recycle column overhead liquid stream is returned to the recycle column 80 as reflux in a line 84. A second portion is intermittently withdrawn from the process through lines 86 and 102 in order to prevent an unacceptable accumulation in the overhead of the recycle column 70 of $C_4$–$C_6$ nonaromatics, which are not removed from the process by the depropanizer 50. A third portion is recycled to the alkylation reactor 20 through the lines 86, 104, 108, 109, 14, and 16. As described previously, this third portion of the recycle column overhead liquid stream admixes with streams flowing in the lines 44, 10, and 14 before entering the alkylation reactor 20. A fourth and final portion of the overhead liquid stream is passed to transalkylation reactor 100 through the lines 86, 104, 106, and 162. As will be described hereinafter, this fourth portion admixes with a stream flowing in a line 158 before entering the transalkylation reactor 100.

A recycle column liquid bottom stream that contains benzene, cumene, DIPB, and heavier alkylated aromatics exits the recycle column 70 in a line 92. A portion of the recycle column bottom stream passes through a line 94, is reboiled in reboiler 90, and returns to the recycle column 70 through the line 96. Another portion of the recycle column bottom stream passes through a line 98 as the cumene column feed stream to cumene column 110.

The cumene column 110 separates the cumene column feed stream into a cumene column overhead stream and a cumene column bottom stream. The cumene column overhead stream comprises cumene and passes through a line 122, a cooler 124, and a line 126, and enters an overhead receiver 120. An overhead liquid stream is withdrawn from the overhead receiver 120 in a line 128. One portion of the overhead liquid stream is refluxed to cumene column 110 through a line 132, and another portion is recovered from the process as the cumene product stream in a line 134. A cumene column liquid bottom stream that contains DIPB and heavier alkylated aromatics exits the cumene column 110 in a line 112. A portion of the cumene column bottom stream passes through a line 114, is reboiled in reboiler 116, and returns to the cumene column 110 through the line 118. Another portion of the cumene column bottom stream passes through a line 136 as the DIPB column feed stream to DIPB column 130.

The DIPB column 130 separates the DIPB column feed stream into a DIPB column overhead stream and a DIPB column bottom stream. The DIPB column overhead stream comprises DIPB and passes through a line 148, a cooler 150, and a line 152, and enters an overhead receiver 160. An overhead liquid stream is withdrawn from the overhead receiver 160 in a line 154. One portion of the overhead liquid stream is refluxed to DIPB column 130 through a line 156, and another portion is passed to the transalkylation reactor 100 through the lines 158 and 162. A DIPB column liquid bottom stream that contains heavier alkylated aromatics exits the DIPB column 130 in a line 138. A portion of the DIPB bottom stream passes through a line 144, is reboiled in reboiler 140, and returns to the DIPB column 130 through the line 146. Another portion of the DIPB column bottom stream is rejected from the process through a line 142 in order to prevent the undesirable accumulation of heavier alkylated aromatics in the process.

Variations on the process flow shown in the drawing may be preferable under certain circumstances. First, if the make-up benzene contains either no water or a relatively small and manageable concentration of water that does not interfere with the operation of the alkylation reactors 20 and 30, then the make-up benzene may be introduced to alkylation reactor 20 rather than to depropanizer 50 as shown in the drawing. Second, if methylpropylbenzene and butylbenzene by-products are formed during alkylation and if these compounds accumulate to concentrations in the overhead of the DIPB column 130 to an extent that the DIPB column overhead liquid stream becomes unacceptable for transalkylation, then the rectification section of the DIPB column 130 can be modified in a manner so that the methylpropylbenzene and butylbenzene by-products are recovered in the overhead receiver 160 and a DIPB-containing stream that is suitable for transalkylation is withdrawn as a sidecut from the DIPB column 130 and passed to the transalkylation reactor 100. In this variation, a portion of the DIPB column overhead liquid stream containing the undesirable methylpropylbenzene and butylbenzene by-products would be returned to the DIPB column 130 as reflux, and the remainder would be rejected from the process.

The beneficial operation of this invention will be further described in the context of an exemplified preferred embodiment which is the alkylation of propylene with benzene to obtain cumene. The description of this invention in terms where preferred embodiment is not meant to limit the claims of this invention to the particular details disclosed herein. The example presented herein is based on engineering calculations and actual operating experience with similar processes.

EXAMPLE

The flowscheme for this example is that shown in the drawing. In describing this example, valves, pumps, feeders, instruments, and heat exchangers other than those necessary for an understanding and appreciation of the invention have been omitted.

Dry propylene feed having a purity of over 99.5 wt-% enters the process in line 12. A benzene-rich stream having a water content of 62 wppm flows in line 109. Water injection enters the process in line 10 and maintains a constant water concentration in the alkylation reactors 20 and 30. The feed stream to the first alkylation reactor 20 is the combination of the benzene-rich stream, the injected water, and the propylene feed. The alkylation reactor effluent in line 18 combines with the propylene feed in line 28 and is passed to alkylation reactor 30. In alkylation reactors 20 and 30, the reactants contact a beta zeolite catalyst at a pressure of from 374 to 442 psi(g) (2579 to 3048 kPa(g)), a temperature of from 322° to 373° F. (161° to 189° C.), a molar ratio of phenyl groups to propyl group of about 4:1, a water concentration of about 554 wppm, and a propylene liquid hourly space velocity of about 0.5 hr$^{-1}$.

100 mass units of liquid alkylation reactor effluent in line 32 having a benzene content of 61.4 wt-% and a water content of 554 wppm enter stripping column 40. The stripping column 40 has eight actual trays and the feed point for the alkylation reactor effluent is above the uppermost tray. At least 96.0 wt-% of the water and 27.2 wt-% of the benzene in the alkylation reactor effluent are removed with the overhead stream in line 34, and less than 10 wt-% of the water in line 34 is recycled to the alkylation reactor 20 with the depropanizer bottom stream, which has a water content of 129 wppm in the line 44. 76.6 mass units of a stripper bottom stream in line 68 enter recycle column 70. 28.6 mass units of a transalkylation reactor effluent in line 88 enter recycle column 70. An overhead stream having a water content of less than 20 wppm is recovered from overhead receiver 80 in line 86. 19.5 mass units of the benzene-containing recycle column overhead stream passes through line 106 and combines with 9.2 mass units of the DIPB-containing DIPB column overhead stream in line 158 that contains essentially nil water, thereby producing a transalkylation reactor feed stream having a water content of less than 20 wppm. In transalkylation reactor 100, the reactants contact a beta zeolite catalyst at a pressure of from 209 to 230 psi(g) (1441 to 1586 kPa(g)), a temperature of about 320° F. (160° C.), a molar ratio of phenyl groups to propyl group of about 2.5:1, a water concentration of less than 20 wppm, and a total liquid hourly space velocity of 0.6 hr$^{-1}$.

Make-up benzene feed having a purity of over 99.5 wt-% and a water content of 151 wppm enters the depropanizer 50 in a line 45. Because the water content of the make-up benzene is subject to unpredictable changes, it is preferred that the make-up benzene be first dried in the depropanizer 60 and then passed via the lines 42 and 44 to the first alkylation reactor 20.

What is claimed is:

1. A process for the production of alkylaromatic hydrocarbons which comprises:

(a) contacting an aromatic feed hydrocarbon and an acyclic feed hydrocarbon with an alkylation catalyst in an alkylation zone at alkylation conditions, reacting said aromatic feed hydrocarbon with said acyclic feed hydrocarbon to produce an aromatic product hydrocarbon in said alkylation zone, and recovering from said alkylation zone an alkylation reaction zone effluent comprising said aromatic feed hydrocarbon, said aromatic product hydrocarbon, polyalkylated aromatic hydrocarbons, and water;

(b) passing said alkylation reaction zone effluent to a stripping column, removing water from said alkylation reaction zone effluent in said stripping column, withdrawing as a bottom stream of said stripping column a stripped alkylation reaction zone effluent comprising said aromatic feed hydrocarbon, said aromatic product hydrocarbon, and said polyalkylated aromatic hydrocarbon, and having a water concentration that is less than the water concentration of said alkylation reaction zone effluent;

(c) passing said stripped alkylation reaction zone effluent and a transalkylation reaction zone effluent comprising said aromatic product hydrocarbon to a separation zone, separating said hydrocarbons in said separation zone into an alkylate stream comprising said aromatic product hydrocarbon and said polyalkylated aromatic hydrocarbon and a first recycle stream comprising said aromatic feed hydrocarbon, and withdrawing said alkylate stream and said first recycle stream from said separation zone;

(d) separating said alkylate stream into a second recycle stream comprising said polyalkylated aromatic hydrocarbon and a product stream comprising said aromatic product hydrocarbon; and, (e) passing at least a portion of said first recycle stream and at least a portion of said second recycle stream to a transalkylation zone containing a transalkylation catalyst at transalkylation conditions comprising a water concentration of less than the water concentration of said alkylation conditions, reacting said aromatic feed hydrocarbon with said polyalkylated aromatic hydrocarbon to produce said aromatic product hydrocarbon in said transalkylation zone, and recovering from said transalkylation zone said transalkylation reaction zone effluent.

2. The process of claim 1 wherein said aromatic feed hydrocarbon comprises benzene and said acyclic feed hydrocarbon comprises ethylene or propylene.

3. The process of claim 1 wherein said alkylation and transalkylation catalysts comprise a zeolite and alumina.

4. The process of claim 3 wherein said catalysts comprise from 10 to 90 wt-% beta zeolite.

5. The process of claim 1 wherein said alkylation conditions are liquid phase and comprise a temperature of from 194° to 518° F. and a pressure of from 150 to 2000 psi(g).

6. The process of claim 1 wherein said transalkylation conditions comprise temperature of from 284° to 500° F. and a pressure of from 150 to 2000 psi(g).

7. The process of claim 1 wherein said alkylation conditions comprise a water concentration of more than 30 wppm.

8. The process of claim 1 wherein said transalkylation conditions comprise a water concentration of no more than 20 wppm.

9. The process of claim 1 wherein a portion of said first recycle stream is contacted with said alkylation catalyst.

10. The process of claim 1 wherein said first recycle stream has a water concentration of less than 20 wppm.

11. The process of claim 1 wherein said stripped alkylation reaction zone effluent contains less than 10 mol-% of the water in said alkylation reaction zone effluent.

12. The process of claim 1 wherein said stripped alkylation reaction zone effluent contains less than 73 mol-% of the aromatic feed hydrocarbon in said alkylation reaction zone effluent.

13. The process of claim 1 wherein said separation zone comprises a zone selected from the group consisting of a rectification column and a fractionation column.

14. The process of claim 1 further characterized in that an overhead stream comprising said aromatic feed hydrocarbon, nonaromatics, and water is withdrawn from said stripping column, said overhead stream is separated into a third recycle stream comprising said aromatic feed hydrocarbon and a reject stream comprising said nonaromatics and water, and at least a portion of said third recycle stream is passed to said alkylation zone.

15. The process of claim 14 wherein said portion of said third recycle stream comprises said aromatic product hydrocarbon.

16. The process of claim 1 wherein at least a portion of said alkylation reaction zone effluent is heated thereby vaporizing said aromatic feed hydrocarbon in said portion of said alkylation reaction zone effluent, and said portion of said alkylation reaction zone effluent after heating is passed to said stripping column.

17. A process for the production of cumene which comprises:

(a) contacting a benzene feed and a propylene feed with an alkylation catalyst comprising beta zeolite in an alkylation zone at alkylation conditions comprising a liquid phase, a temperature of from 302° to 518° F., a pressure of from 150 to 2000 psi(g), and a water concentration of at least 30 wppm, reacting benzene and propylene to produce cumene in said alkylation zone, and recovering from said alkylation zone an alkylation reaction zone effluent comprising benzene, cumene, diisopropylbenzene, heavier alkylated aromatic hydrocarbons, and water;

(b) passing said alkylation reaction zone effluent to a stripping column, removing water from said alkylation reaction zone effluent in said stripping column, withdrawing as a bottom stream of said stripping column a stripped alkylation reaction zone effluent comprising benzene, cumene, diisopropylbenzene, and said heavier alkylated aromatic hydrocarbons, and containing less than 10 mol-% of the water and less than 73 mol-% of the benzene in said alkylation reaction zone effluent;

(c) passing said stripped alkylation reaction zone effluent and a transalkylation reaction zone effluent comprising cumene to a first fractionation column, separating said hydrocarbons in said first fractionation column into an alkylate stream comprising cumene, diisopropylbenzene, and said heavier alkylated aromatic hydrocarbons, and a first recycle stream comprising benzene, and withdrawing said alkylate stream and said first recycle stream from said first fractionation column;

(d) passing at least a portion of said first recycle stream to said alkylation zone;

(e) passing said alkylate stream to a second fractionation column, separating said hydrocarbons in said second fractionation column into an intermediate separation stream comprising said diisopropylbenzene and said heavier aromatic hydrocarbons and a product stream comprising cumene, and withdrawing said intermediate separation stream and said product stream from said second fractionation column;

(f) passing said intermediate separation stream to a third fractionation column, separating said hydrocarbons in said third fractionation column into a second recycle stream comprising diisopropylbenzene and a heavy aromatic stream comprising said heavier alkylated aromatic hydrocarbons, and withdrawing said second recycle stream and said heavy aromatic stream from said third fractionation column; and, (g) passing at least a portion of said first recycle stream and at least a portion of said second recycle stream to a transalkylation zone containing a transalkylation catalyst comprising beta zeolite at transalkylation conditions comprising a temperature of from 392° to 500° F., a pressure of from 150 to 2000 psi(g), and a water concentration of less than 20 wppm, reacting in said transalkylation zone benzene and diisopropylbenzene to produce cumene, and recovering from said transalkylation zone said transalkylation reaction zone effluent.

18. The process of claim 17 further characterized in that an overhead stream comprising benzene, propane, and water is withdrawn from said stripping column, said overhead stream is passed to a depropanizer column wherein said hydrocarbons and water are separated into a third recycle stream comprising benzene, a first reject stream comprising propane, and a second reject stream comprising water, said third recycle stream, said first reject stream, and said second reject stream are withdrawn from said depropanizer column, and at least a portion of said third recycle stream is passed to said alkylation zone.

19. The process of claim 17 further characterized in that said stripped alkylation reaction zone effluent is passed to a rectification column, said hydrocarbons are separated into a fourth recycle stream comprising benzene and a rectified stripped alkylation reaction zone effluent comprising benzene, cumene, diisopropylbenzene, and said heavier alkylated aromatic hydrocarbons, withdrawing said fourth recycle stream and said rectified stripped alkylation reaction zone effluent from said rectification column, passing at least a portion of said fourth recycle stream to said alkylation zone or said transalkylation zone, and passing said rectified stripped alkylation reaction zone effluent to said first fractionation column.

20. The process of claim 17 wherein at least a portion of said stripped alkylation reaction zone effluent is heated thereby vaporizing benzene in said portion of said stripped alkylation reaction zone effluent, and said portion of said stripped alkylation reaction zone effluent after heating is passed to said stripping column.

* * * * *